(12) United States Patent
Luo et al.

(10) Patent No.: US 8,481,968 B2
(45) Date of Patent: Jul. 9, 2013

(54) ELECTRON MICROSCOPE SPECIMEN AND METHOD FOR PREPARING THE SAME

(75) Inventors: Jian-Shing Luo, Taoyuan County (TW); Wen-Shan Hsu, Taoyuan County (TW)

(73) Assignee: Inotera Memories, Inc., Hwa-Ya Technology Park Kueishan, Taoyuan (TW)

( * ) Notice: Subject to any disclaimer, the term of this patent is extended or adjusted under 35 U.S.C. 154(b) by 265 days.

(21) Appl. No.: 12/954,916

(22) Filed: Nov. 29, 2010

(65) Prior Publication Data

US 2011/0291008 A1    Dec. 1, 2011

(30) Foreign Application Priority Data

Jun. 1, 2010 (TW) ................................ 99117585 A (51) Int. Cl.
   *G21K 5/00* (2006.01)
   *H01J 37/26* (2006.01)

(52) U.S. Cl.
   USPC ...... 250/440.11; 250/307; 250/310; 250/311; 250/492.3

(58) Field of Classification Search
   USPC ............ 250/306, 307, 309, 310, 311, 440.11, 250/442.11, 492.1, 492.3
   See application file for complete search history.

(56) References Cited

U.S. PATENT DOCUMENTS

| | | | |
|---|---|---|---|
| 6,942,033 B2 | 9/2005 | Brooks | |
| 7,482,587 B1 | 1/2009 | Finch | |
| 2004/0056195 A1* | 3/2004 | Kuhlman et al. | 250/307 |
| 2004/0201324 A1* | 10/2004 | Takeuchi et al. | 310/328 |
| 2008/0067385 A1* | 3/2008 | Tokuda et al. | 250/310 |
| 2010/0090108 A1* | 4/2010 | Hoeche | 250/307 |
| 2011/0011190 A1* | 1/2011 | Subramaniam | 73/866.5 |

* cited by examiner

*Primary Examiner* — Nicole Ippolito
(74) *Attorney, Agent, or Firm* — Winston Hsu; Scott Margo (57) ABSTRACT

A method for preparing an electron microscope specimen is provided. The method includes providing a wafer sample with an analysis region disposed thereon. A dicing process is performed to cut a sample piece from the wafer sample. The sample piece includes a target pillar structure wherein the analysis region is located on a top portion of the target pillar structure. A thinning process is performed to thin the top portion of the target pillar structure. The invention further provides an electron microscope specimen and a method of forming a 3D image.

15 Claims, 9 Drawing Sheets

ELECTRON MICROSCOPE SPECIMEN AND METHOD FOR PREPARING THE SAME

BACKGROUND OF THE INVENTION

1. Field of the Invention

The present invention relates to an electron microscope specimen and the preparing method thereof, and more particularly, to an electron microscope specimen which is suitable for constructing a three-dimensional image and the preparing method thereof.

2. Description of the Prior Art

With the miniaturization of semiconductor devices, the analysis techniques for observing the microstructure of semiconductor devices have become increasingly important. For example, the microstructure of the semiconductor devices can be observed by using a scanning electron microscopy (SEM) or a transmission electron microscopy (TEM). Due to the better resolution, TEM is widely used in analyzing semiconductor devices.

However, as the integration of semiconductor devices are upgrading and various semiconductor devices with special structure are proposed, current two-dimensional image analysis techniques are unable to reflect the device structure precisely, especially those devices with high curvature structure, for example, via structures. Therefore, the industry is developing a three-dimensional image technology which can retrieve two-dimensional (2D) images of the specimen from different angles and further construct a three-dimensional (3D) image out of the 2D images. Consequently, the real structure image of the product can be obtained.

Figure 1:
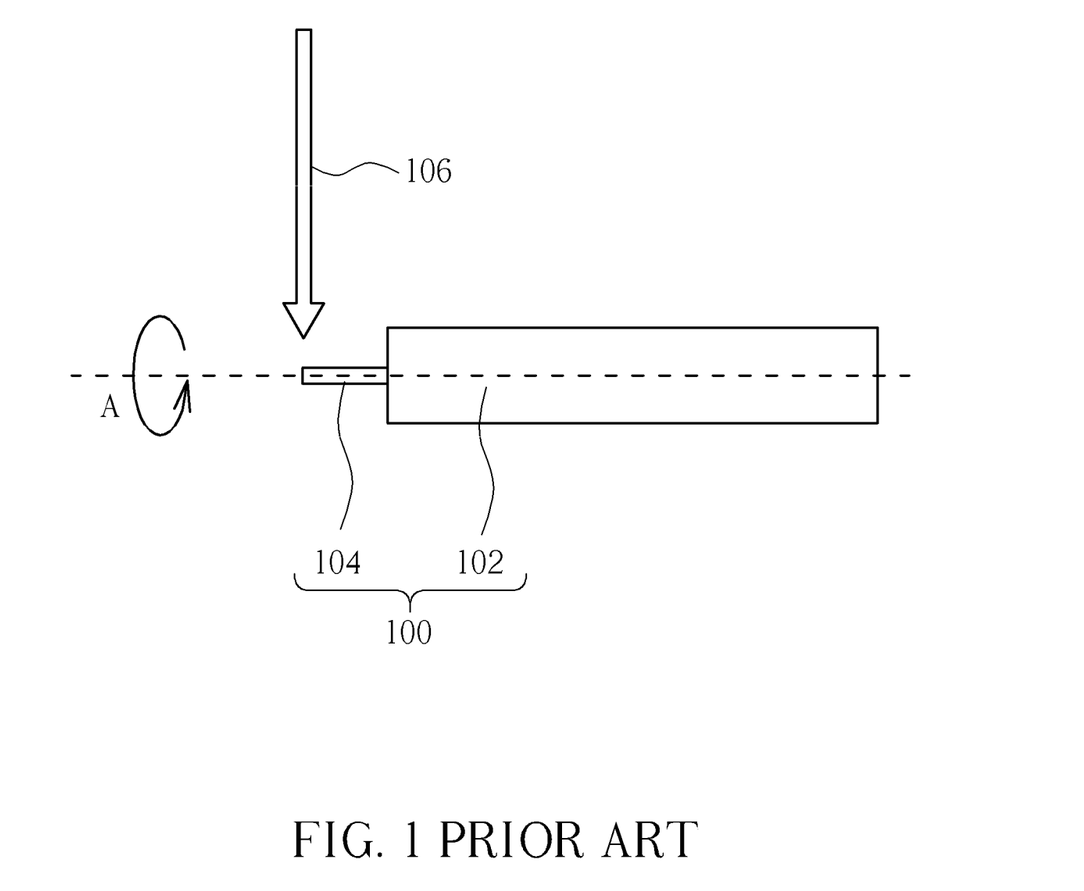
FIG. 1 and FIG. 2 are schematic diagrams showing the structure of the 3D image specimen according to conventional art.
Figure 2:
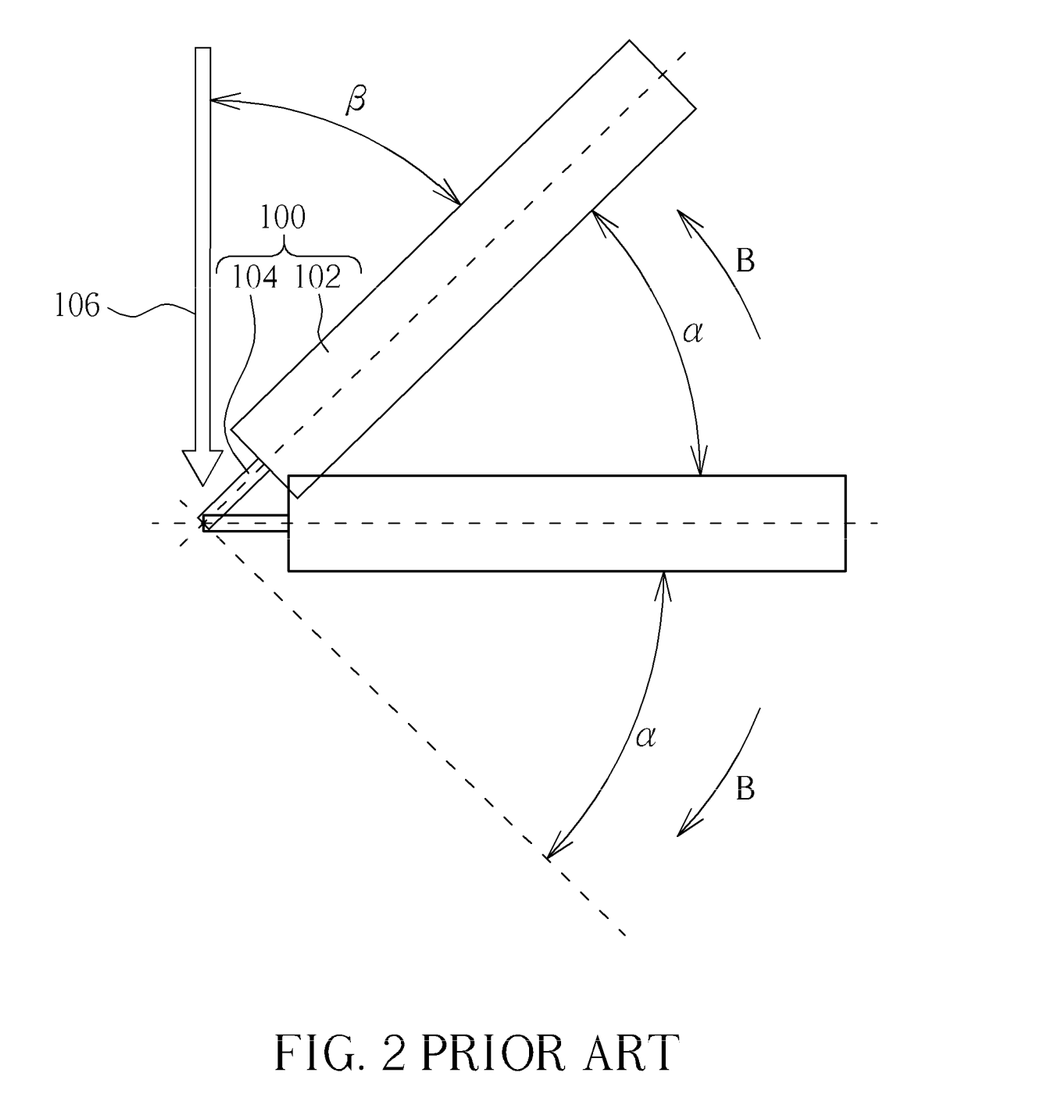

Since the 3D image must be constructed by retrieving 2D images from different angles of the specimen, special configuration of the specimen is required. FIG. 1 and FIG. 2 are schematic diagrams showing the structure of the specimen for 3D image according to conventional art. As shown in FIG. 1, the specimen 100 includes a base portion 102 and a sample 104. The sample 104 protrudes from the base portion 102 to form a pillar structure. By using an electron beam 106 of the electron microscope, the wafer structure or microstructure of the sample 104 can be detected and observed. In order to retrieve the images from different angles, the specimen 100 is rotated along the axis in the direction of arrow A. Alternatively, as shown in FIG. 2, the specimen 100 can be tilted along the direction of arrow B between the angle α and the angle −α to collect more 2D images.

However, the conventional design of the base portion 102 and the sample 104 has an inherent limitation, which is also known as missing-wedge phenomenon. The missing-wedge phenomenon occurs, when the specimen 100, for example, is tilted beyond the angle α (usually 45 degrees). In such case, the images of the sample 104 cannot be captured by the electron microscope because the electron beam 106 is obstructed by the base portion 102, resulting in a nearly 45-degree missing wedge. As the thickness of the base portion 102 and the height of the sample 104 have both reached their critical values, it is difficult to overcome 45-degree threshold. Therefore, there is a strong need in this industry to provide an improved electron microscope specimen and the preparing method to resolve the above mentioned problems.

SUMMARY OF THE INVENTION

It is one objective of the present invention to provide an electron microscope specimen and the preparing method thereof in order to overcome the above mentioned problem such as missing wedge phenomenon that occurs when constructing a 3D image according to conventional art.

The present invention, in one aspect, provides a method for preparing an electron microscope specimen. First, a wafer sample having thereon an analysis region is provided. A dicing process is performed to cut a sample piece from the wafer sample. The sample piece includes a target pillar structure wherein the analysis region is located on a top portion of the target pillar structure. A thinning process is performed to thin the top portion of the target pillar structure.

The present invention, in another aspect, further provides a method for forming a 3D image. First, a specimen is provided. The specimen is prepared by the above mentioned method. Then, an image retrieving process is performed to capture a plurality of 2D images of the specimen from different angles by using a microscope. Lastly, the plurality of 2D images are constructed to form the 3D image.

The present invention, in still another aspect, further provides an electron microscope specimen. The electron microscope specimen includes a holder and a sample piece disposed thereon. The sample piece includes a base portion, a pillar structure and a tip portion. The pillar structure is disposed on the base portion, and a ladder structure is formed between the pillar structure and the sample base. The tip portion is located on the pillar structure, and an analysis region is disposed on the tip portion.

By using a dicing process and a thinning process in the present invention, a specimen with superior structure can be obtained. The problem of missing wedge resulted from the obstruction of the sample base in conventional arts can be prevented.

These and other objectives of the present invention will no doubt become obvious to those of ordinary skill in the art after reading the following detailed description of the preferred embodiment that is illustrated in the various Figures and drawings.

DETAILED DESCRIPTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Figure 3:
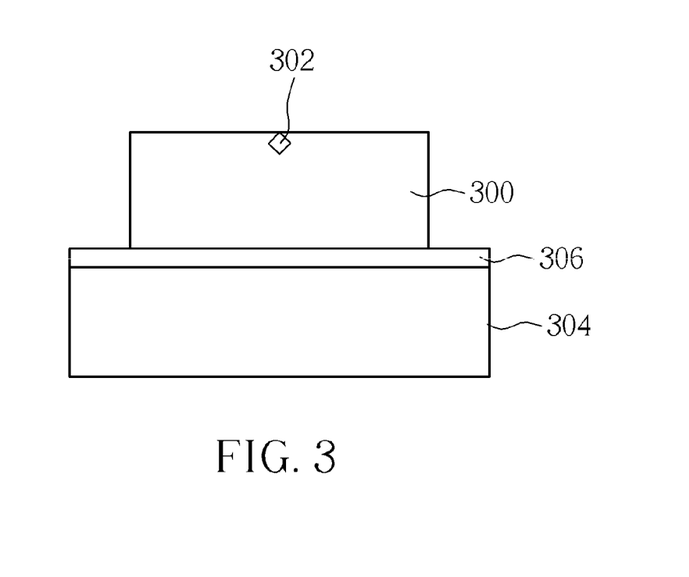
FIG. 3 to FIG. 10 are schematic diagrams showing the method for preparing the electron microscope specimen according to the present invention.

FIG. 3 to FIG. 10 are schematic diagrams showing the method for preparing the electron microscope specimen according to one embodiment of the present invention. As shown in FIG. 3, a wafer sample 300 is provided. An analysis region (or an analysis spot) 302 is defined on the surface of the wafer sample 300. Microstructures to be analyzed are located in the analysis region 302. The wafer sample 300 is preferably a semiconductor wafer piece. However, the wafer sample 300 may be any material that can be observed by the electron microscope, for example, a biological material, a biological chip or other materials.

Subsequently, the wafer sample 300 is attached onto an auxiliary sample 304. According to one embodiment of the present invention, the wafer sample 300 is adhered onto the auxiliary sample 304 by an adhesion layer 306. Preferably, the adhesion layer 306 is a heat meltable layer, such as a wax layer or a hot melt resin, but should not be limited thereto. In one embodiment, the auxiliary sample 304 is also a wafer. In another embodiment, the auxiliary sample 304 can be any material that can support the wafer sample 300. Preferably, the hardness of the auxiliary sample 304 is close to that of the wafer sample 300.

Figure 4:
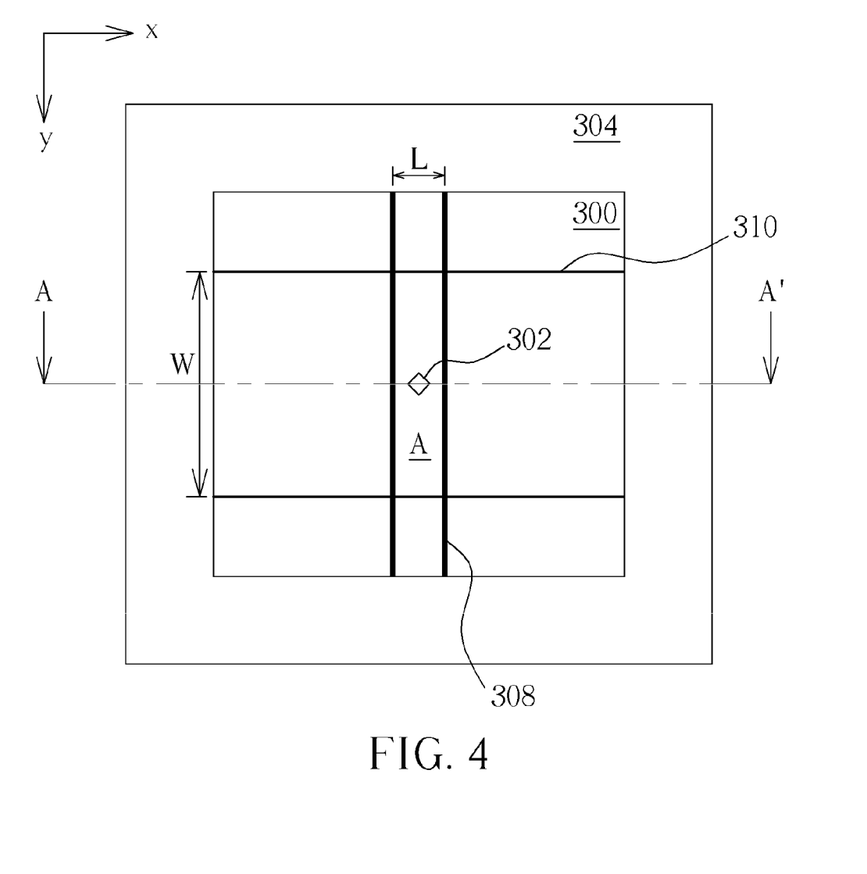
Figure 5:
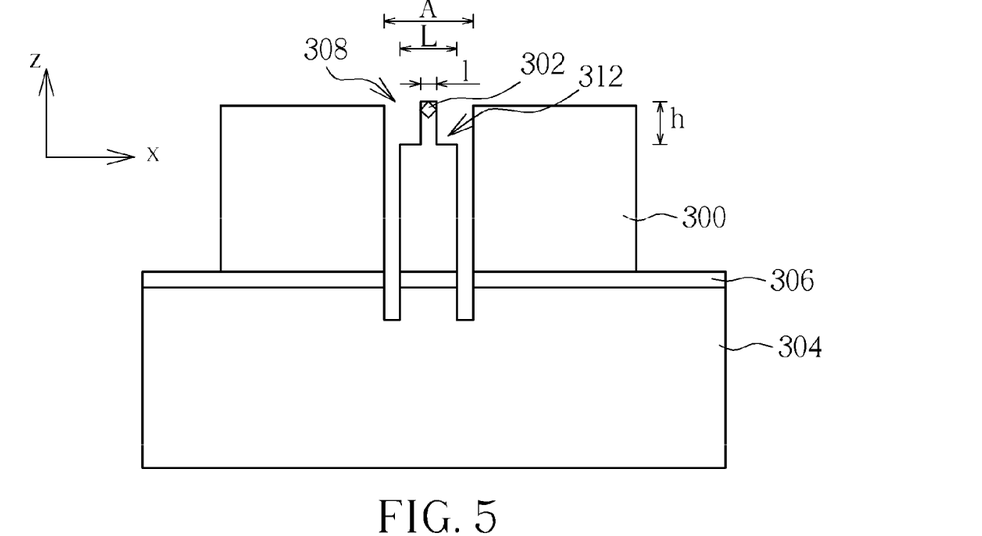

Please refer to FIG. 4 and FIG. 5. FIG. 5 is a cross sectional view taken along line AA' of FIG. 4. Subsequently, a first dicing process is performed. The first dicing process may utilize a blade or a laser process, for example. Two first dicing trenches 308 and two second dicing trenches 310 are formed on the wafer sample 300. The analysis region 302 is disposed in an area A, which is encompassed by the two first dicing trenches 308 and the two second dicing trenches 310. In one embodiment of the present invention, the first dicing trenches 308 are parallel to each other, and the second dicing trenches 310 are parallel to each other. The first dicing trenches 308 are substantially perpendicular to the second dicing trenches 310, thereby forming the rectangular area A. In another embodiment, the first dicing trenches 308 may be not perpendicular to the second dicing trenches 310, thereby forming a parallelogram area A. In still another embodiment, the first dicing trenches 308 are not parallel to each other, and the second dicing trenches 310 are not parallel to each other, as lone as a closed region A can be formed between the first dicing trenches 308 and the second dicing trenches 310.

As shown in FIG. 5, by utilizing single dicing process or multiple dicing processes, a recessed ladder structure 312 is formed between two first dicing trenches 308. The dimension of the ladder structure 312 can be determined by a length L, a length l, and a height h. A width W of the ladder structure 312 is determined by the two second dicing trenches 310. The length L, the length l, the height h and the width W, which determine the dimension of the ladder structure 312, will be discussed in more detail later. In the present embodiment, the depth of the first dicing trench 308 and the depth of the second dicing trench 310 are both greater than the height of the wafer sample 300. More specifically, the first dicing trench 308 and the second dicing trench 310 both extend into the adhesion layer 306 and may be recessed into the auxiliary sample 304.

Figure 6:
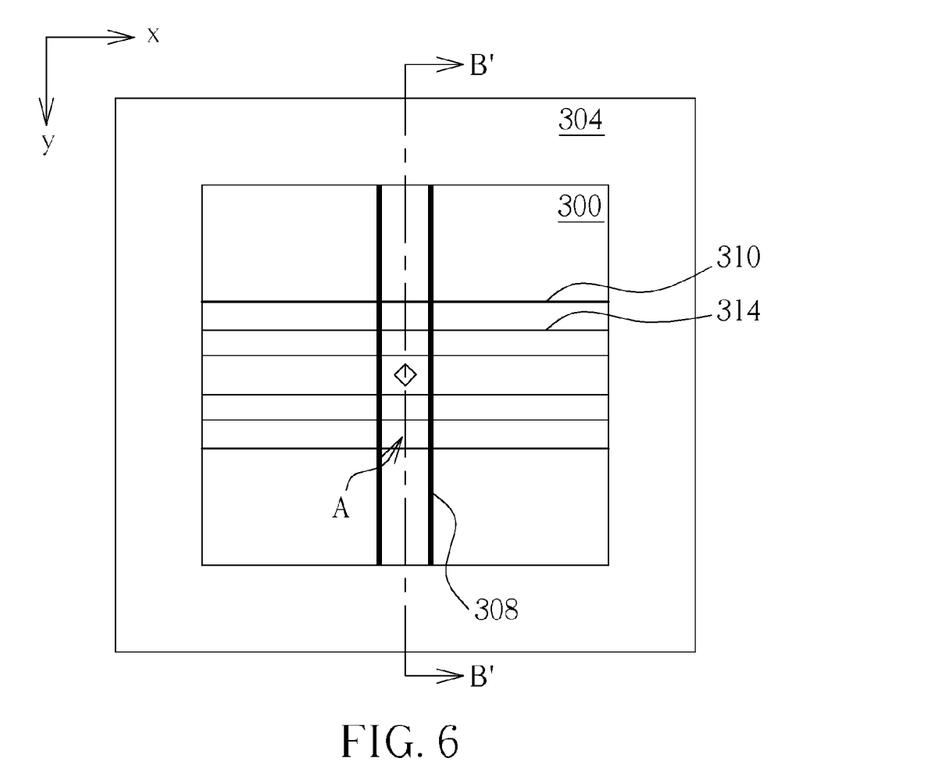
Figure 7:
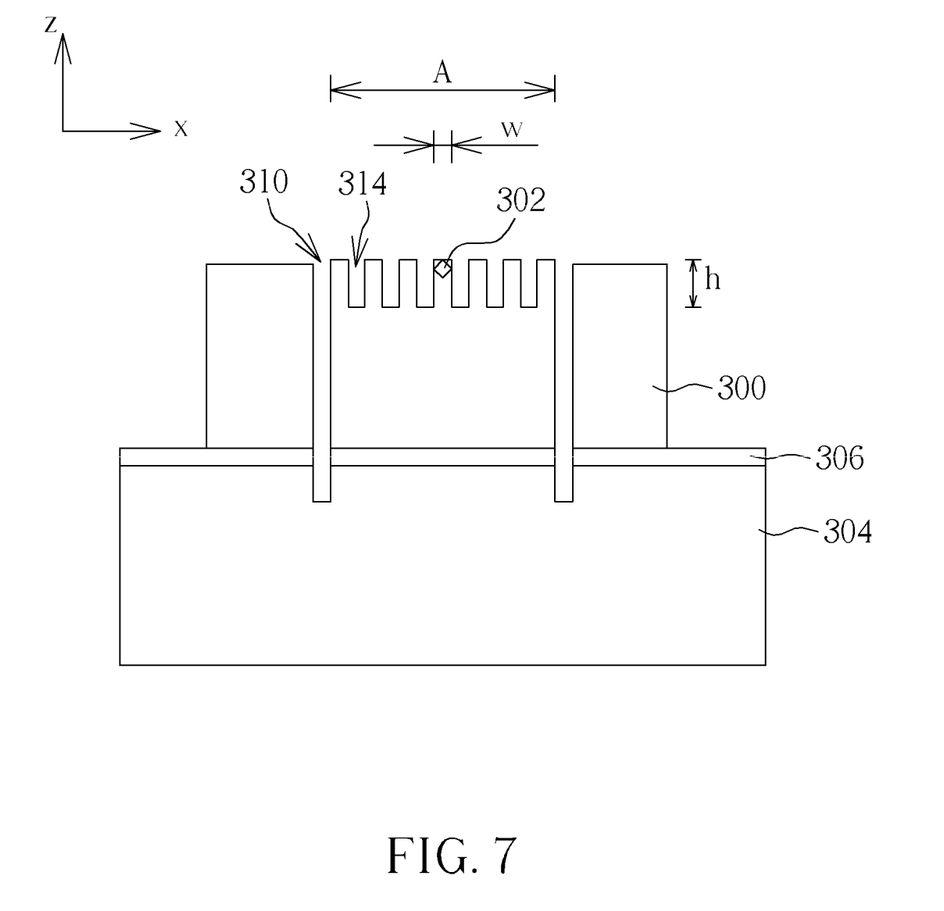

Referring now to FIG. 6 and FIG. 7, a second dicing process is then performed, wherein FIG. 7 is a schematic, cross-sectional view taken along line BB' of FIG. 6. A plurality of line-shaped third dicing trenches 314 are formed on the wafer sample 300 between the two second dicing trenches 310 in the second dicing process. In one embodiment of the present invention, the third dicing trenches 314 are parallel to each other. The intervals between any two of the third cutting trenches 312 are substantial the same. The depth of each of the third cutting trenches 312 is substantially equal to the height h of the ladder structure 312. After performing the first dicing process and the second dicing process, a heating process is carried out to melt the adhesion layer 306 such that area A portion of the wafer sample 300 can be detached from the auxiliary sample 304. The detached area A portion of the wafer sample 300 becomes a sample piece 316 to be tested or analyzed.

Figure 8:
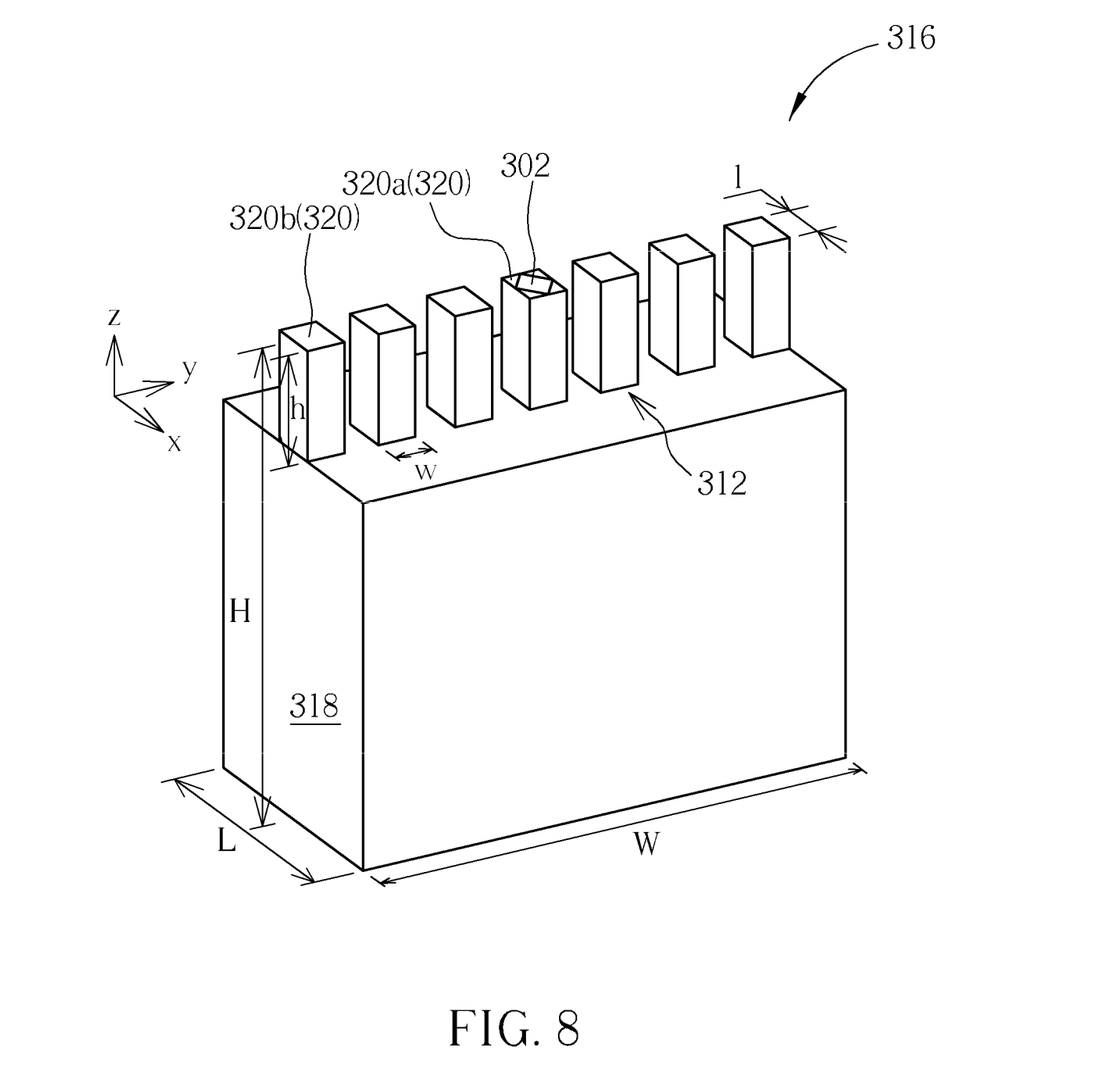

Referring to FIG. 8, a 3D schematic view of the sample piece according to one embodiment of the present invention is demonstrated. The sample piece 316 includes a base portion 318 and a plurality of pillar structures 320. Each pillar structure 320 upwardly protrudes from the base portion 318. The ladder structure 312 is formed between each pillar structure 320 and the base portion 318, such that the pillar structures 320 are similar to a parapet in battlement-shape on the base portion 318. The dimension of the sample piece 316 is determined by the length L, the width W and a height H, while the dimension of each pillar structure 320 is determined by the length l, a width w and the height h. The above-mentioned length L, width W, height H and length l, width w, height h can be determined by the first dicing trenches 308, the second dicing trenches 310 and the third dicing trenches 314. For example, during the first dicing process, as shown in FIG. 5, the length L of the sample piece 316, and the length l, the height h of the pillar structure 320 are determined by the first dicing trenches 308. As shown in FIG. 4, the width W of the sample piece 316 are determined by the second dicing trenches 310. During the second dicing process, as shown in FIG. 7, the width w of the pillar structure 320 is determined by the third dicing trenches 314. In one preferred embodiment of the present invention, the length l and the width w of the pillar structure 320 are substantially the same and the value thereof are the smaller the better, but are not limited thereto. In one embodiment of the present invention, for example, the length L of the sample piece 316 is about 90 micrometers (μm), the width W is about 2 millimeter (mm) and the height H is about 780 μm. The length l of the pillar structure 320 is about 40 μm, the width w is about 40 μm, and the height h is about 150 μm. As shown in FIG. 8, the analysis region 302 is located on one of the pillar structures 320, namely the target pillar structure 320a. The other pillar structures 320 are dummy pillar structures 320b. Preferably, the target pillar structure 320a is the middle one of the pillar structures 320.

Figure 9:
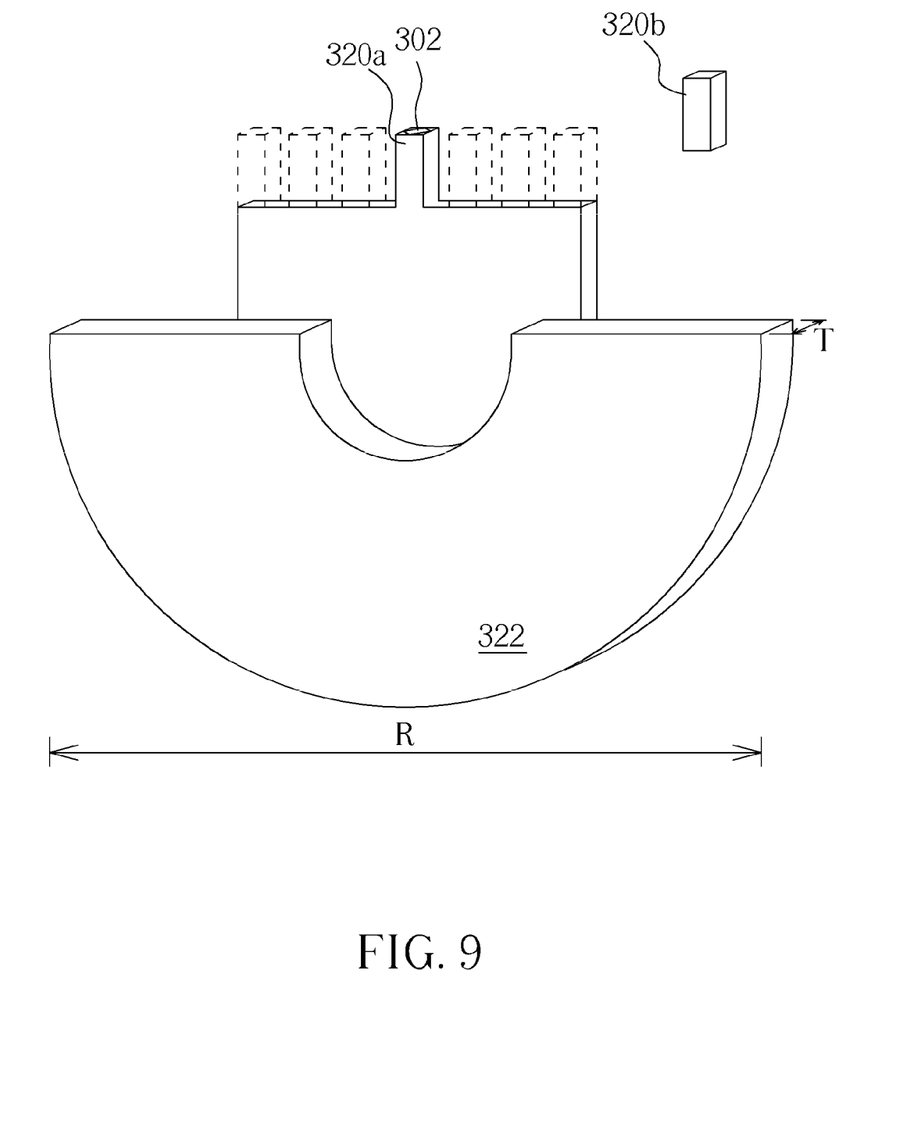

As shown in FIG. 9, the sample piece 316 is then affixed to a holder, for example, a metal half ring 322. In one embodiment of the present invention, the diameter R of the metal half ring 322 is about 3 mm, and the thickness T of the metal half ring 322 is about 0.04 mm. The sample piece 316 and the metal half ring 322 can be combined by using a resin or other adhesive materials. Next, the dummy pillar structures 320b, which do not contain the analysis region 302, are removed, while retaining the target pillar structure 320a with the analysis region 302. In one embodiment, the dummy pillar structures 320b can be removed manually by using a metal needle when examined under a microscope.

Figure 10:
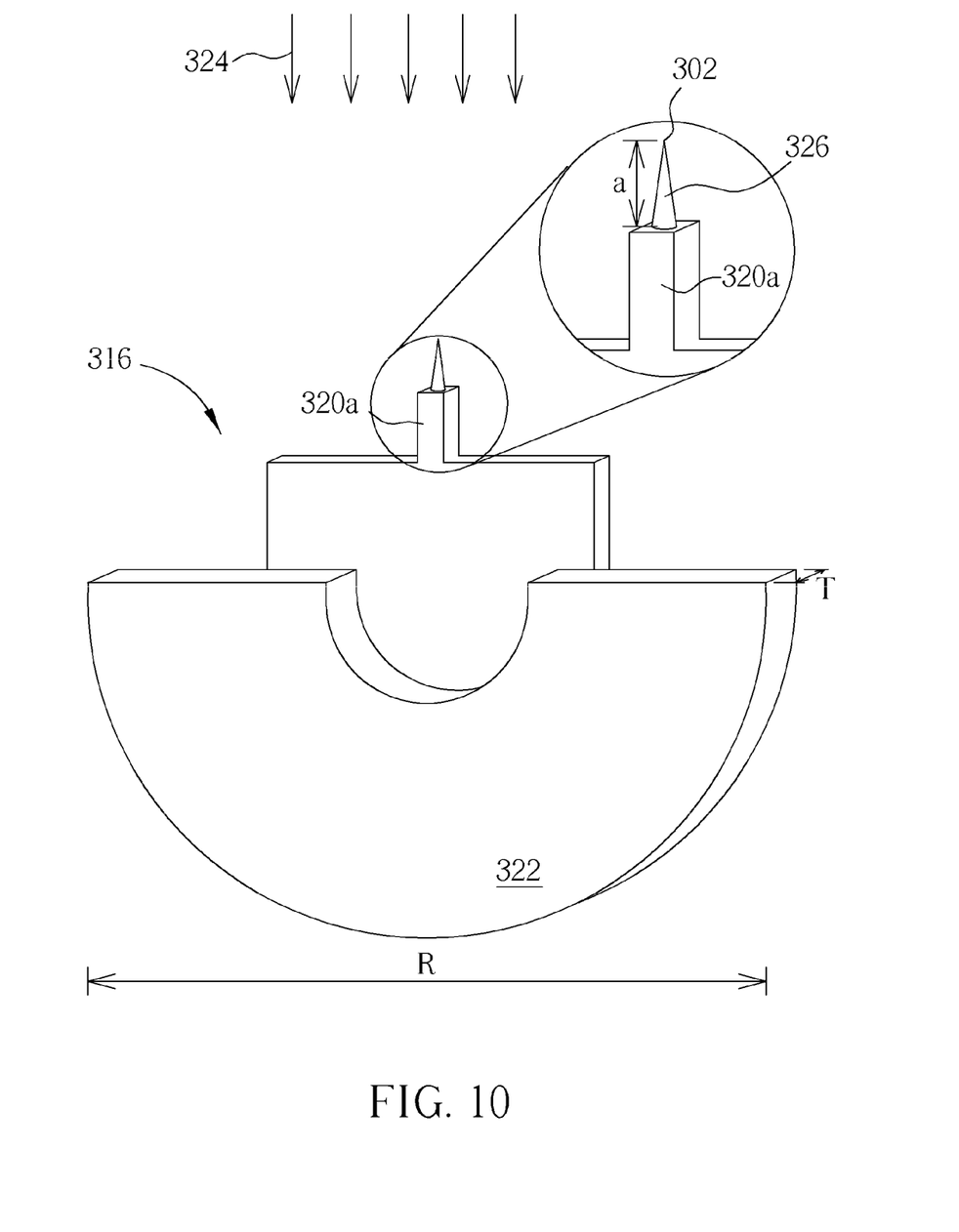

As shown in FIG. 10, a thinning process 324 is performed. For example, a focus ion beam (FIB) is used to trim down the target pillar structure 320a to a tip portion 326, wherein the analysis region 302 is disposed on top of the tip portion 324. In one embodiment of the present invention, a protective layer (not shown) can be formed on the target pillar structure 320a before the thinning process. The protective layer is preferably a metal film such as a platinum film, a tungsten film or other suitable materials which can prevent damage of the analysis region 302 during the thinning process 324. The tip portion 326 has a tip height a. In one embodiment of the present invention, the tip height a is about 60 μm. The fabrication of an electron microscope specimen 328 is completed.

Figure 11:
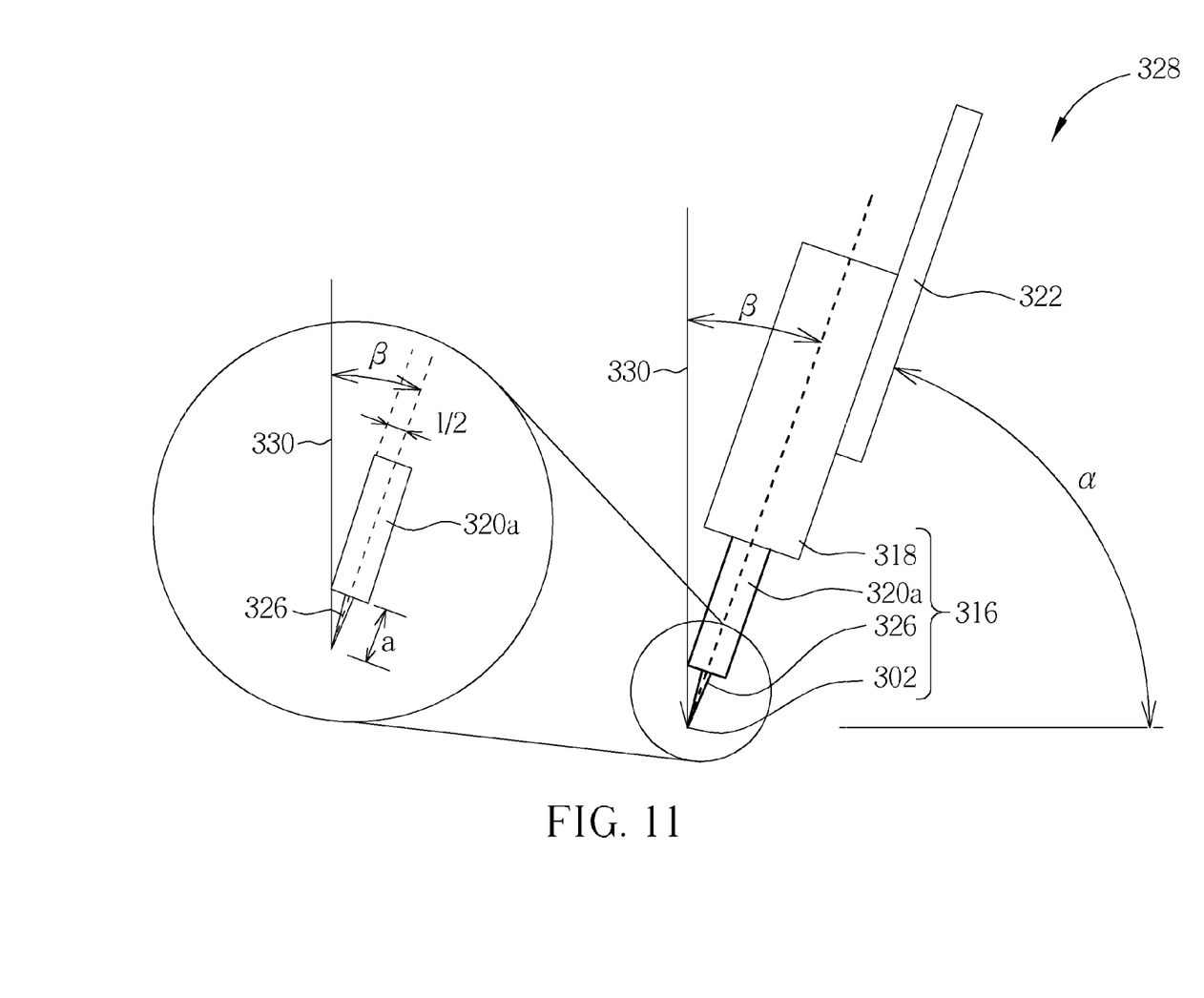
FIG. 11 is a schematic diagram of the specimen under the electron microscope according to the present invention.

The 2D images of the analysis region 302 on the specimen 328 can be retrieved by the electron microscope from different angles and a 3D image can be constructed by these 2D images through a software computing. FIG. 11 is a schematic diagram of the specimen under the electron microscope according to one embodiment of the present invention. As shown in FIG. 11, the specimen 328 of the present invention has a larger viewing angle α when the specimen 328 is tilted and/or rotated in the electron microscope (compared with FIG. 2). An enlarged view of a portion of the specimen 328 is illustrated on the left side of FIG. 11 in the circled region. In one preferred embodiment, the tip height a of the tip portion 326 is about 60 μm, while the half of the height h of the pillar structure 320a (l/2) is about 20 μm. The angle β between the electron beam 330 and the tip portion 326 is about 20 degrees. That is, the specimen 328 of the present invention can provide a viewing angle α which is at least 70 degrees. Comparing to conventional art which has a viewing angle of about 45 degrees, the present invention can effectively alleviate the missing wedge problem. Considering the limitation of the tilting angle of the objective lens in the electron microscope, in one embodiment of the present invention, the ratio of half of the length l (l/2) and the tip height a of the target pillar structure 320a, namely tan β, is less than 0.35 (β=20°). Preferably, tan β is substantially between 1 (β=45°) and 0.35 (β=20°). Accordingly, the ratio of the length l and the tip height a of the target pillar structure 320a is substantially between 2 and 0.7.

To sum up, the method of preparing an electron microscope specimen in the present invention uses a dicing process and a thinning process to form the novel pillar structure and the tip portion of the specimen. A larger viewing angle can be obtained and the phenomenon of missing wedge can be alleviated when constructing 3D images. Because the dicing process is employed in the present invention, comparing to conventional specimen manufacturing method which uses FIB, the method in the present invention is more rapid and the shape of the specimen can be well controlled.

Those skilled in the art will readily observe that numerous modifications and alterations of the device and method may be made while retaining the teachings of the invention.

What is claimed is:

1. A method for preparing an electron microscope specimen, comprising:
   providing a wafer sample having thereon an analysis region;
   performing a dicing process to cut a sample piece from the wafer sample, wherein the sample piece comprises a target pillar structure and the analysis region is located on a top portion of the target pillar structure, wherein the dicing process comprises performing a first dicing process to form two first dicing trenches and a recessed ladder structure, performing a second dicing process to form two second dicing trenches on the wafer sample, wherein a height and a length of the target pillar structure are defined by the first dicing trenches; and performing a third dicing process to form a plurality of third dicing trenches between the two second dicing trenches, wherein a width of the target pillar structure is defined by the third dicing trenches, wherein a depth of each of the first dicing trenches and a depth of each of the second dicing trenches are both greater than a height of the wafer sample; and
   performing a thinning process to thin the top portion of the target pillar structure.

2. The method for preparing an electron microscope specimen according to claim 1, wherein the length is substantially equal to the width.

3. The method for preparing an electron microscope specimen according to claim 1, wherein the third dicing process further comprises forming a plurality of dummy pillar structures.

4. The method for preparing an electron microscope specimen according to claim 3 further comprising: removing the dummy pillar structures after the third dicing process.

5. The method for preparing an electron microscope specimen according to claim 1, wherein a depth of each of the third dicing trenches is substantially equal to the height of the target pillar structure.

6. The method for preparing an electron microscope specimen according to claim 1 further comprising: affixing the sample piece to a holder after performing the dicing process.

7. The method for preparing an electron microscope specimen according to claim 6, wherein the holder comprises a metal half ring.

8. The method for preparing an electron microscope specimen according to claim 1 further comprising: adhering the sample piece onto an auxiliary sample before performing the dicing process.

9. The method for preparing an electron microscope specimen according to claim 8 further comprising: performing a heating process to detach the sample piece from the auxiliary sample after the dicing process.

10. The method for preparing an electron microscope specimen according to claim 1 further comprising: forming a protective layer on the target pillar structure before performing the thinning process.

11. The method for preparing an electron microscope specimen according to claim 10, wherein the protective layer comprises metal.

12. The method for preparing an electron microscope specimen according to claim 1, wherein the thinning process comprises using a focus ion beam.

13. The method for preparing an electron microscope specimen according to claim 1, wherein the thinning process comprises forming a tip portion on the top portion of the target pillar structure, wherein the analysis region is located on the tip portion.

14. The method for preparing an electron microscope specimen according to claim 13, wherein the tip portion comprises a tip height, and wherein a ratio of the length of the target pillar structure to the tip height is substantially between 2 to 0.7.

15. A method for forming a 3D image, comprising:
   providing a specimen which is prepared by the method of claim 1;
   performing an image retrieving process to capture a plurality of 2D images of the specimen from different angles by using a microscope; and
   constructing the plurality of 2D images to form the 3D image.

* * * * *